United States Patent [19]
Biggs

[11] 4,264,211
[45] Apr. 28, 1981

[54] LIGHT SENSOR

[75] Inventor: William W. Biggs, Lincoln, Nebr.

[73] Assignee: Li-cor, Inc., Lincoln, Nebr.

[21] Appl. No.: 32,712

[22] Filed: Apr. 23, 1979

[51] Int. Cl.³ .................... G01N 21/01; G01B 11/28
[52] U.S. Cl. .................................. 356/432; 250/227;
356/213; 356/222; 356/380
[58] Field of Search ............... 356/432, 379, 380, 215,
356/222, 414, 213; 250/227; 350/96.1, 96.15,
96.16, 96.2

[56] References Cited
U.S. PATENT DOCUMENTS

| | | | |
|---|---|---|---|
| 2,360,663 | 10/1944 | Eddy | 250/227 |
| 3,060,319 | 10/1962 | Greunke | 250/227 |
| 3,317,738 | 5/1967 | Piepenbrink et al. | 250/227 |
| 3,980,893 | 9/1976 | Merlen | 250/227 |
| 4,004,152 | 1/1977 | Obser et al. | 356/431 |

FOREIGN PATENT DOCUMENTS

382048 8/1973 U.S.S.R. .................... 250/572

*Primary Examiner*—John K. Corbin
*Assistant Examiner*—Bruce Y. Arnold
*Attorney, Agent, or Firm*—Vincent L. Carney

[57] ABSTRACT

To measure the density of a foilage canopy, an elongated average-light measuring instrument includes an elongated diffuser, an elongated quartz rod with a uniform diffusing groove in it between it and the diffuser and a photodiode at one end so that radiation hitting the diffuser enters the quartz rod and is transmitted to the photodiode to provide a measure of average light entering the length of the instrument. To digitize light instead of sensing average light, another embodiment includes a plurality of separate light entrances positioned along the length of the quartz rod and a scanner that scans across the rod or a uniform diffusing groove and circuitry that digitizes the electrical signal from the photodiode periodically in accordance with the position of the light scanner on the groove.

34 Claims, 4 Drawing Figures

LIGHT SENSOR

This invention relates to radiation measuring instruments and more particularly to average-radiation measuring instruments useful in measuring average radiation over a given length or to digital radiation measuring instruments which are useful in measuring the area of individual objects such as leaves.

In one class of average-radiation measuring instrument, an individual photodiode measures the radiation and converts it to electricity which is measured. The intensity of the radiation, as measured by the signals generated by the photodiode, can correlate to a physical or physiological phenomenon. Similarly, in one class of digital radiation measuring instrument for individual leaves or like objects, a beam of radiation is scanned across the object as it moves with respect to the scanner such as on a conveyor. The radiation which is not blocked by the object is collected and passed to a photodiode, which generates an electrical signal, which indicates the presence or absence of a portion of the leaf or other opaque object, and thus the area of such a leaf or opaque object can be determined.

In one type of prior art instrument of this class for measuring average radiation, individual radiation sensors which include a diffuser, filter, and photodiode are positioned to receive the radiation at a single spot. In another type of prior art measuring instrument of this type, an elongated thermopile with an elongated filter has been used. Other elongated instruments of undisclosed structure have been published in the art. In another embodiment, an individual sensor is physically moved back and forth on a track in order to measure average radiation.

The prior art single point sensing instruments have the disadvantage of being subject to errors because they are positioned in a particularly shady or illuminated location and thus do not measure average radiation. Thermopiles have the disadvantage of being direction sensitive and not being able to precisely filter the radiation to achieve a specific spectral response. The prior art area measuring devices for a single object such as a leaf have the disadvantages of including relatively complicated scanners and of being expensive.

Accordingly, it is an object of the invention to provide a novel average-radiation sensor.

It is a further object of the invention to provide a novel radiation sensor for use in a scanner of an area measuring instrument for leaves or the like.

It is a still further object of the invention to provide a radiation sensor which is simple in construction and economical because of the need for only a single filter and photodiode.

It is a still further object of the invention to provide a radiation sensor which is not direction sensitive to the instrument.

It is a still further object of the invention to provide an average-radiation sensor in which the spectral sensitivity range to radiation may be changed by simply changing a single small filter or a single detector.

It is a still further object of the invention to provide an area measuring sensor which provides a digital output with a simple structure.

It is a still further object of the invention to provide a radiation sensor with equal sensitivity response along a length of the sensor.

In accordance with the above and other objects of the invention, an average-radiation measuring instrument includes an average-radiation sensor having an elongated radiation conductor with a diffusing groove along one surface. A radiation diffuser for cosine response is positioned above the radiation conductor and a filter and photodiode are positioned at one end of the radiation conductor.

The diffuser for cosine response is referred to as an eye and serves to transmit radiation into a reflective compartment for the conductor. The diffusing groove in the conductor also serves as a diffuser which permits radiation to enter the rod. It is referred to as a radiation-conductor entrance.

To provide equality in the sensitivity to radiation of the instrument along its length, the photodiode is positioned with a lens between it and the end of the rod to intercept a cone of radiation that provides such equality of response. Generally, this cone angle is selected to minimize nonuniformity with respect to loss of radiation from entrance of the radiation to its reception by the photodiode. The loss of radiation is related to the path of the radiation in the conductor and especially to the percentage of radiation lost from the conductor through the radiation-conductor entrance which is a predetermined percentage of its circumference along its length.

The loss through the entrance is related to bounces of radiation rays that hit the entrance. The number of bounces of radiation is determined by the length and diameter of the rod and the angle of incidence of the radiation. For a rod of one centimeter diameter and one meter of length, the maximum cone angle in the preferred embodiment is approximately thirty degrees inside the rod for a radiation-rod entrance extending along the length of the rod and covering about two percent of its circumference. The angle leaving the rod will be different.

The response changes between two points on the sensor along its length is related to the pitch of the radiation which is related to the number of times the radiation impinges back onto the diffusing groove per unit length of the sensor. In this applica- the pitch of the radiation is the length of rod required for the radiation to return in its path (usually screw shaped) to the same angular position around the circumference of the conductor.

Because the precision of the equality of the response along the length is obtained by selecting the radiation at an angle that permits statistically fewer opportunities for radiation to impinge upon the diffusing groove, this equality is obtained at the expense of sensitivity and should be selected for the application. If the precise equality along the sensor length is not needed but increased radiation sensitivity is needed, then the photodiode should collect the radiation using as large a cone angle as possible and to collect a maximum amount of radiation. Less equality of sensitivity with respect to length is needed for digital instruments than analogue.

To further improve the uniformity of sensitivity response along its length, the diffusing groove is altered along its length by increasing the sensitivity by widening it or reducing the sensitivity by covering parts of the diffusing groove with radiation absorbing material such as india ink. The end of the rod opposite to the photodiode is roughened and then covered with a radiation absorber to absorb radiation. This is done because it is costly to provide a reflective surface at this end which provides uniform behavior with time and from conductor to conductor.

The elongated radiation conductor may be inserted under a plant canopy of foliage and the radiation passing through the foliage along the length of the diffuser enters the radiation conductor along its longitudinal diffusing groove. The radiation conductor conducts the radiation to the end where it passes through a single filter onto a photodiode and thus is converted to an electrical signal which is measured or recorded to indicate the average radiation passing through the foliage and therefore the amount of foliage cover.

In another embodiment, a radiation measuring instrument includes a digital radiation sensor, the radiation conductor, having a plurality of separate distinct diffusing entrances positioned along its length opposite the diffusing groove with opaque sections in between. A conveyor or the like moves the leaves between the sensor and a scanning beam of radiation to generate radiation pulses along the length where the leaf does not block the radiation. Radiation from the pulses pass along the length of the conductor to a sensor at the end where they are converted to electrical pulses which, when subtracted from the maximum number of pulses available, indicate the area of the leaf being passed between the scanning beam and the sensor.

It is known in the prior art to use a radiation conductor with a diffusing groove along its length for radiation to enter it in conjunction with a scanning device. However, such apparatuses have not been used together with replaceable filters or individual diffusing entrances which make thems suitable for either measuring canopy cover of foliage or the area of individual leaves or other opaque objects.

A smooth quartz rod has been used as an average-radiation sensor to determine its effectiveness. Data was gathered and published indicating the density of a canopy but the structure of the instrument was not published and its reliability questionable since the sensor operated by accident because, unknown to the manufacturer and use, fingerprints permitted radiation to enter the radiation conductor. No proper structure was included to admit radiation. The apparatus was not understood and development later yielded the claimed structure.

From the above description it can be understood that the average-radiation measuring instrument of this invention has several advantages such as: (1) it is simple in construction and economical; (2) it is not direction sensitive and yet measures radiation across a length to provide an average reading of the radiation; (3) it can be simply adjusted for different radiation ranges by changing a single filter and/or detector; and (4) its sensitivity is substantially the same at each location along its length. The digital radiation measuring instrument of this invention has the advantages of providing a digital output with a relatively simple apparatus and a single radiation sensor.

The above noted and other features of the invention will be better understood from the following detailed description when considered in conjunction with the accompanying drawings, in which.

Figure 1:
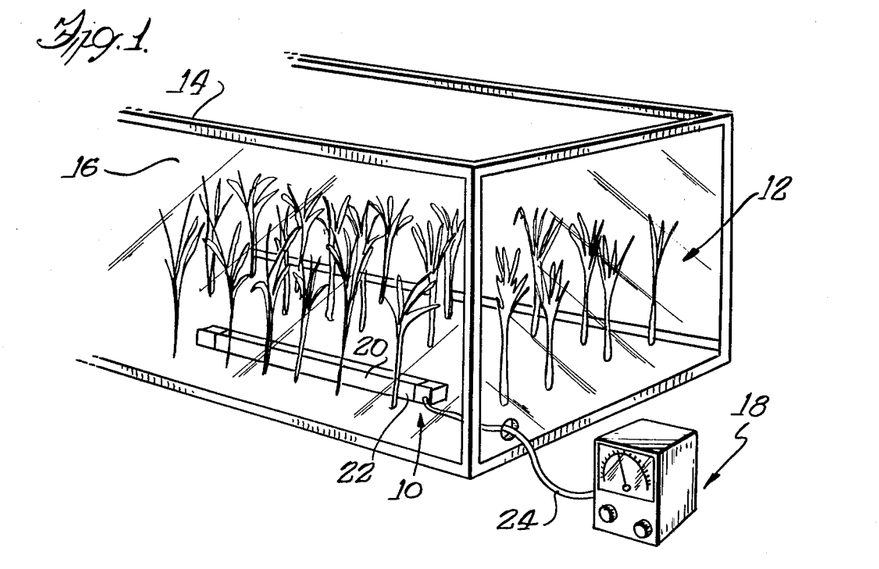
FIG. 1 is a perspective view of an embodiment of the invention.

In FIG. 1, there is shown an average-radiation sensor 10, a bed of plants 12, a portion of a greenhouse frame 14, transparent members 16 of a greenhouse and a meter 18. The average-radiation sensor 10 is electrically connected to the meter 18 by a cord 24 to form an average-radiation measuring instrument. The average-radiation sensor 10 is intended to sense radiation of the type that can be guided by a radiation conductor or wave guide such as visible light and infrared radiation.

To measure the density of the foliage canopy formed by the plants 12, the average-radiation sensor 10 is positioned against the bottom of the bed of the plants 12 so that it lies underneath their foliage. The plants 12 are within the greenhouse formed of framing members 14 and windows 16 so that sunlight shines through the windows 16 and the foliage 12 onto the average-radiation sensor 10. The meter 18 is an ammeter calibrated in appropriate units to indicate radiation and thus indicates the average radiation passing through the foliage 12 from a source of radiation.

The average-radiation sensor 10 is approximately 47 inches long and one inch by one inch in cross-section. It has a light diffusing top 20 and a photoelectric assembly 22 on one end. Along its length is a radiation conductor (not shown in FIG. 1) which conducts the radiation passing through the diffuser 20 to the photoelectric assembly 22, where it is converted to an electric signal. The electric signal is conducted through a cord 24 to the radiation meter 18, where it is indicated.

Because the average-radiation sensor 10 is elongated, the average radiation passing through the foliage 12 across the length of the average-radiation sensor is measured rather than only the radiation at a small point, thus giving a better indication of the density of the foliage. Of course, a recorder or recording radiation meter or other type of electrically-actuated measuring instrument may be substituted for the meter 18.

Figure 2:
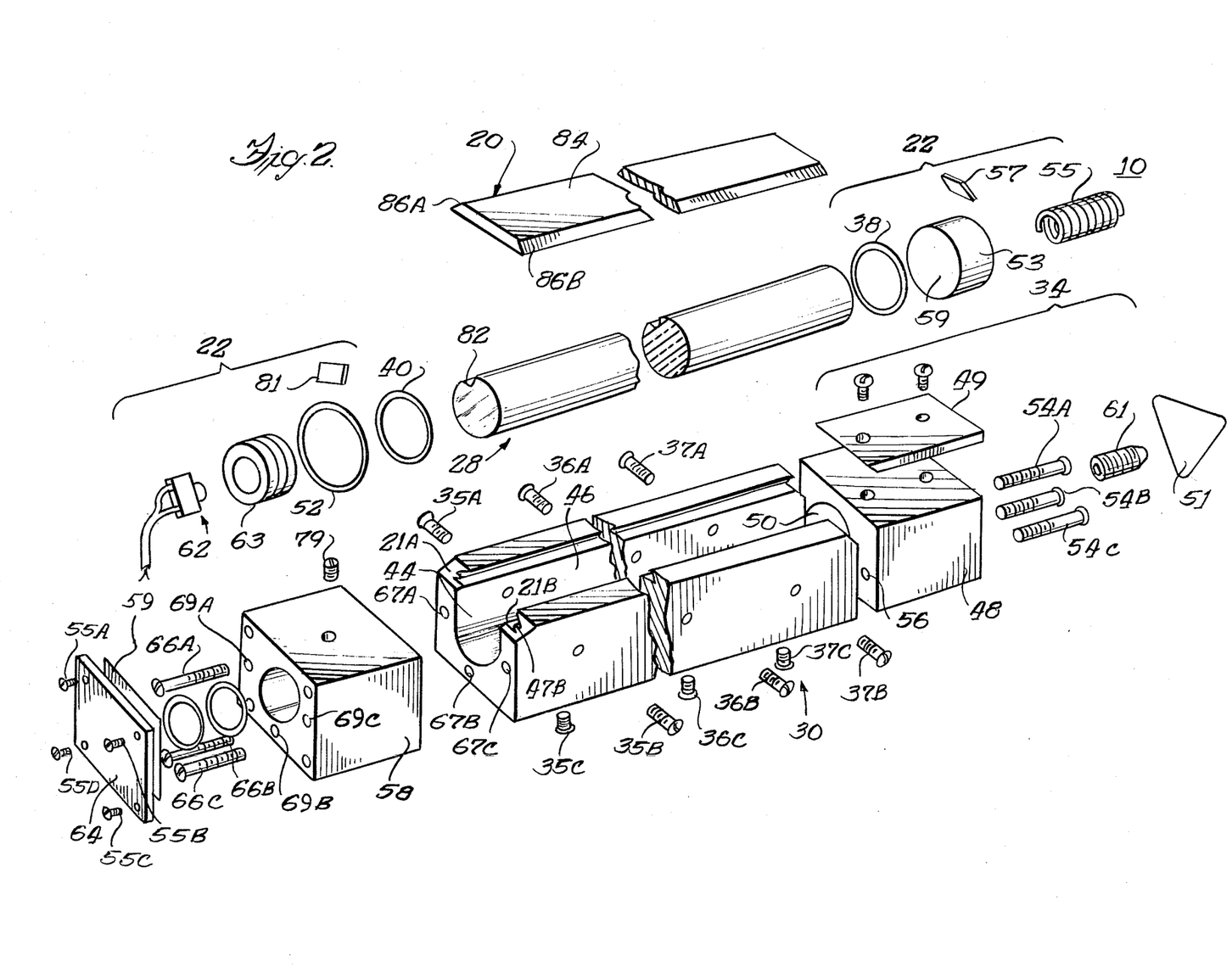
FIG. 2 is an exploded perspective view of a portion of the embodiment of FIG. 1, with portions broken away.

In FIG. 2, there is shown an exploded perspective view, partly broken away, of the average-radiation sensor 10, the principal parts of which are: a diffuser eye 20, a cylindrical quartz rod 28, an aluminum housing 30, and a photoelectric assembly 22, with the quartz rod 28 serving as the internal radiation conductor of the average-radiation sensor 10.

One end of the housing 30 is sealed by an end piece assembly 34 and the other end by the photoelectric assembly 22. To support the quartz rod 28 at its center and first and second ends, three sets of three set screws 35A–35C, 36A–36C and 37A–37C support the rod 28 along its length. Also first and second O-rings 38 and 40 each support a different one of the two opposite ends of the quartz rod 28 end piece assembly 34 and photoelectric assembly 22. The top of the housing is closed by the diffuser eye 20. The diffuser eye may be a pleriglas sheet of the type sold by Rohm and Haas Company, Independence Mall West, Philadelphia, PA 19105, under the designation W-7328 Acrylic.

The aluminum housing 30 has the basic shape of an elongated, right, regular parallelopiped and is formed of a square aluminum bar. It is approximately 45 inches long and has a one inch by one inch square cross-section. At each of its opposite ends, aligned with its longitudinal axis, are first and second openings 42 and 44 to receive the opposite ends of the quartz rod 28, with the first opening 42 being closed by the end member 34 and the second opening 44 being closed by the photoelectric assembly 22. Along the top surface of the housing 30 is a longitudinal slot 46 adapted to be covered by the diffuser eye 20 and having along each inner side inwardly cut bottom tracks 47A and 47B and upper sealant grooves 21A and 21B. The bottom tracks 47A and 47B are adapted to receive corresponding ones of the complimentarily formed edges 86A and 86B of the diffuser eye 20. A sealant is placed in the upper grooves 21A and 21B to overlie the edges of the eye 20. The diffuser 20 is exactly one meter long to provide one meter of active sensor length and is 0.4 inches wide.

The end member 34 includes a spring housing 48, a sensor face cap 49, and a nose cone 51. The spring housing 48 is shaped substantially as a right regular parallelopiped with a cylindrical opening 50 having substantially the same width as the opening 42 in the housing 30. The cylindrical opening 50 is sufficiently large to receive the O-ring 38 with one end of the quartz rod 28 within it. Two tapped holes extend through the sensor face cap 49 and into the top of the spring housing 48 to mount the face cap 49 on the spring housing 48 and over the edge of the housing 30 and diffuser eye 20 as explained below.

The spring housing 48 of the end member 34 has the same rectangular outside dimensions as the housing 30 against which it fits, with the cylindrical opening 50 being aligned with the generally cylindrical opening of slot 42. It is held thereto by three screws 54A-54C which fit within aligned holes in the spring housing 48 and the one end of the housing 30, the holes in the end of the housing 30 being tapped. One of the holes through the spring housing being shown at 56.

Reflection of light from this end is difficult to control without precisely ground surfaces. It has been found that such reflection is not conducive to a predictable representation of the average radiation impinging upon the average-radiation sensor 10 from sensor to sensor or across a period of time with the same sensor.

The end of the quartz rod 28 within the spring housing 48 is roughened and coated with a light absorbing material to absorb light.

To hold the quartz rod 28 against the end piece assembly 34, the end piece assembly 34 includes a plastic spring cup 53, a coil compression spring 55 and a diffuser eye end gasket 57. The plastic spring cup 53 has a flat circular end 59, which fits against the end of the rod 28 and cylindrical side walls defining a cup to receive the spring 55. The spring cup 53 and spring 55 fit within the opening 50 in the spring housing 48 between the end of the quartz rod 28 and the end member 34. The cone 51 is mounted to the end of the spring housing 48 by the threaded stud 61 to provide a pointed end for insertion of the sensor 10 into foliage.

To convert the average radiation to an electric signal for transmission through cord 24 to the radiation measuring instrument 18 (FIG. 1), the photoelectric assembly 22 includes a cylindrical radiation-conductor spacer 52, a photoelectric cell housing 58 and an end plate 64. The cylindrical radiation-conductor spacer 52 fits into one end of the housing 58 and the end plate 64 closes the other end of the housing 58.

The photoelectric cell housing 58 is sized to fit against the end of the housing 30 to provide a uniform elongated housing, and has for this purpose, dimensions in cross-section of one inch by one inch. It is mounted to the end of the housing 30 by screws 66A-66C which pass through tapped holes 67A-67C in the side of the housing after passing through holes 69A-69C in the photoelectric cell housing 58.

To support the quartz rod 28, an opening in the photoelectric cell housing 58 is of such a size as to receive the O-ring 40 and the quartz rod 28 and is aligned with the longitudinal axis of the quartz rod 28. Within the housing photoelectric cell 58 is a photoelectric cell assembly 62 of a conventional design that is electrically connected to the cord 24 (FIG. 1). It includes a photodiode, photocell or other photosensor for converting the radiation to an electric signal. Between the photoelectric cell assembly 62 and the end of the quartz rod 28 are two black plastic rings and a lens and filter assembly 63 which select the band of radiation to be received and focus radiation from a thirty degree cone of the radiation leaving the quartz rod 28 onto the diode. An expansion gasket 81 is positioned between the end of the diffuser eye 20 and the overhanging edge of the detector housing to hold the eye in place at one end.

The photoelectric cell assembly receives radiation from the end of the quartz rod 28 and converts the radiation into electrical signals which are transmitted through the cord 24. The photoelectric cell assembly 62 fits into the housing 58 and is held in place by a set screw 79 extending through the top wall of the detector housing. A flat sensor end cap 64 is mounted thereto by screws 55A-55D. Between the sensor end cap 64 and the end of the housing 58 is a sheet of double-stick tape 59 for weather-proof sealing.

The photoelectric cell assembly 62 includes within it the appropriate optical system and transducer to focus the radiation and select the frequency. Generally the filter passes radiation of between 400 and 700 nanometers and usually includes an interference filter. This range is of particular use with measurements in the agricultural field, but of course for other applications, other filters may be used.

To support the center portion of the quartz rod 28 between the O-ring 38 and 40 within the aluminum housing 30, the three sets of screws 35A-35C, 36A-36C and 37A-37C are spaced longitudinally along the housing 30 to be threaded into tapped holes in it for screws 35A, 36A and 37A are in one side of the housing, the holes for screws 35B, 36B and 37B in the other side and 35C, 36C and 37C in the bottom to contact the quartz rod 28 with their tips so as to hold it in place. The screws are plastic tipped so as to not scratch the quartz rod 28.

The inner surface of the housing 30 is reflective. To obtain the reflective inner surface of the housing 30, the housing is coated with white reflective coating such as white reflective coating (Cat. No. 6080) composed of barium sulfate, a binder and a solvent. Such a coating may be purchased from Eastman Kodak Company, Rochester, N.Y. 10650.

While a rectangular housing 30 is shown, the housing may, of course, be cylindrical or need not even be complete across its length but the quartz rod 28 would operate with simply an end sensor. Nonetheless, the housing 30 aids in efficiency and convenience of use as a packaging component to mount the quartz rod 28 properly with respect to the diffuser 20 and the photoelectric assembly 22 and to shield it from stray radiation. It is also believed that efficiency is increased by the reflective coating on the inner surface of the housing.

To receive radiation along a one-meter length and conduct it to the photoelectric assembly 22, the quartz rod 28 is 45 inches long and includes a polished surface and ends. Its diameter is approximately 10 millimeters. Suitable fused quartz rods may be purchased from Amersil Inc., 685 Ramsey Avenue, Hillside, N.J. 07205. A rod having 150 grit has been found to be suitable in terms of optical finish.

To enable radiation to enter the quartz rod 28 along one edge, facing the diffuser 20 and diametrically opposite to the bottom of the housing 30, a diffusing groove 82 is ground along the length of the quartz rod 28. Radiation entering the diffusing groove is captured by the quartz rod 28 which acts as a radiation conductor and conducts a portion of the radiation to the end adjacent to the photoelectric assembly 22.

While a diffusing groove is ground in the preferred embodiment to provide a rough surface to diffuse and thus admit radiation to the conductor, any other deformation may be used provided that it has a predetermined pattern which can be used to correlate incident radiation on the diffuser to radiation entering the conductor. Indeed, it has been found that fingerprints or imperfections in the surface admit radiation but of course any kind of cut, printing or roughness along the surface will permit radiation to enter. A uniform diffusing groove has been found most suitable for purposes of uniformity and ease in fabrication. The diffusing groove may also be used as an aligning surface for visual alignment of the rod or alignment with a fixture.

To provide cosine response of the radiation conducted by the quartz rod 28, the diffuser eye 20 is a pleriglas plate which diffuses radiation impinging upon it. It includes two beveled side edges 86A and 86B which fit within a corresponding two bottom side tracks 47A and 47B of the housing 30, the top tracks 21A and 21B being for a seal. A flat upper portion 84 has a width of approximately 0.4 inches and is approximately 45 inches long. The short ends are beveled or ramped upwardly to be held by the complimentarily undercut housing 58 and end housing 48.

Geometrically, it is possible for radiation to hit the photodiode without being captured by the radiation conductor if it impinges on the instrument near the diode. If it is in line with the photodiode it may strike it without being conducted by the radiation conductor.

Failure to block this radiation increases the sensitivity at this end of the average-radiation sensor 10. For this reason, the diffusing groove 82 extends in the preferred embodiment only 4 or 5 inches from the end of the conductor so that the quartz rod serves only as a radiation conductor at that end and does not receive new radiation. Also, a radiation opaque member covers the diffuser eye 20 over the last 4 or 5 inches near the photodiode to block line-of-sight or direct radiation to the photodiode.

Before using the average-radiation sensor 10, it is assembled with the quartz rod within the housing 30 (FIG. 2), its center portion held by screws 35A–35C, 36A–36C and 37A–37C, one end being within the O-ring 38 resting within the end of the housing 48 and the other end within the O-ring 40 within the housing 58. The housing 58 is fastened to the housing 30 with its beveled edge overhanging the quartz rod 28.

Before fastening the quartz rod tightly in place, the diffusing groove 82 in the quartz rod 28 is oriented upwardly so that a plane passing through it bisects the bottom of the housing 30 and the diffuser 20 perpendicularly. The uniformity of the detector is corrected by directing a colliminated light beam into the groove and measuring the intensity of radiation. The groove is touched up by scratching to increase the sensitivity or with india ink to decrease sensitivity from the sensor end to the other end to provide uniformity. This may also be done in a test fixture rather than in the housing. After the quartz rod and the housing 58 have been adjusted with the diffuser in place, the diffuser eye 20 is sealed within the tracks of the housing 30 to have its end underlie the beveled edge of the housing 58 and the end housing 48 fastened in place with the sensor face cap holding the diffuser.

The diffuser groove 82 may be oriented in other positions and still function, but it is difficult to correct for linearity. Moreover, its sensitivity changes with orientation by creating the optical effect of magnifying the diffusing groove to radiation being transmitted into it. Moreover, it is possible to measure cylindrical irradiance by using a separate cylindrical diffuser surrounding the radiation conductor to transmit radiation to the diffusing groove.

While a quartz rod is used in the preferred embodiment other radiation conductors may be used. However, it is advantageous for the conductor to be radiation passing rather than opaque. Thus, radiation not captured by the conductor upon incidence passes through it so that, upon scattering or reflection on the other side, radiation may impinge on the conductor at a different angle and be captured by it.

In use, the cord 24 (FIG. 1) is connected to a meter 18 and to the average-radiation sensor 10 (FIG. 1). The average-radiation sensor 10 is inserted in the foliage in a typical application so that it extends its full length into the foliage with the meter 18 being positioned for convenient reading.

To determine the amount of cover provided by the foliage, radiation shining from a source such as through the glass panes of a greenhouse as shown in FIG. 1 passes through the foliage and impinges upon the average-radiation sensor 10. The radiation impinges on the diffuser eye 20, which passes diffused radiation into the housing 30 and into the quartz rod 28 through the diffusing groove 82. The housing tends to reflect the radiation so that a maximum amount enters the diffusing groove 82 and radiation hitting the sides of the quartz rod 28 is either reflected back against the housing or passes through the rod and is reflected by the housing.

Radiation entering the diffusing groove 82 passes along the quartz rod 28, which serves as a radiation conductor, to the photoelectric assembly 22 which converts it into an electric signal related to intensity and transmits the electric signal through the electric cord 24 to the meter 18. The radiation intensity may be taken as a measure of the foliage density since it correlates to the foliage density. A recording instrument may be used to record changes in cover across a period of time or an integrator may be attached to integrate the signals, if desired.

When used in this manner, the average-radiation sensor 10 has the advantages over the prior art of providing readings of the cover averaged over an area and thus minimizing errors that might occur from density of foliage in one place which are not representative of the entire foliage. Moreover, it is portable and provides economical and reasonably-precise measurements. While the average-radiation sensor 10 is intended primarily for use in measuring radiation, it may be used for other purposes as well.

Figure 3:
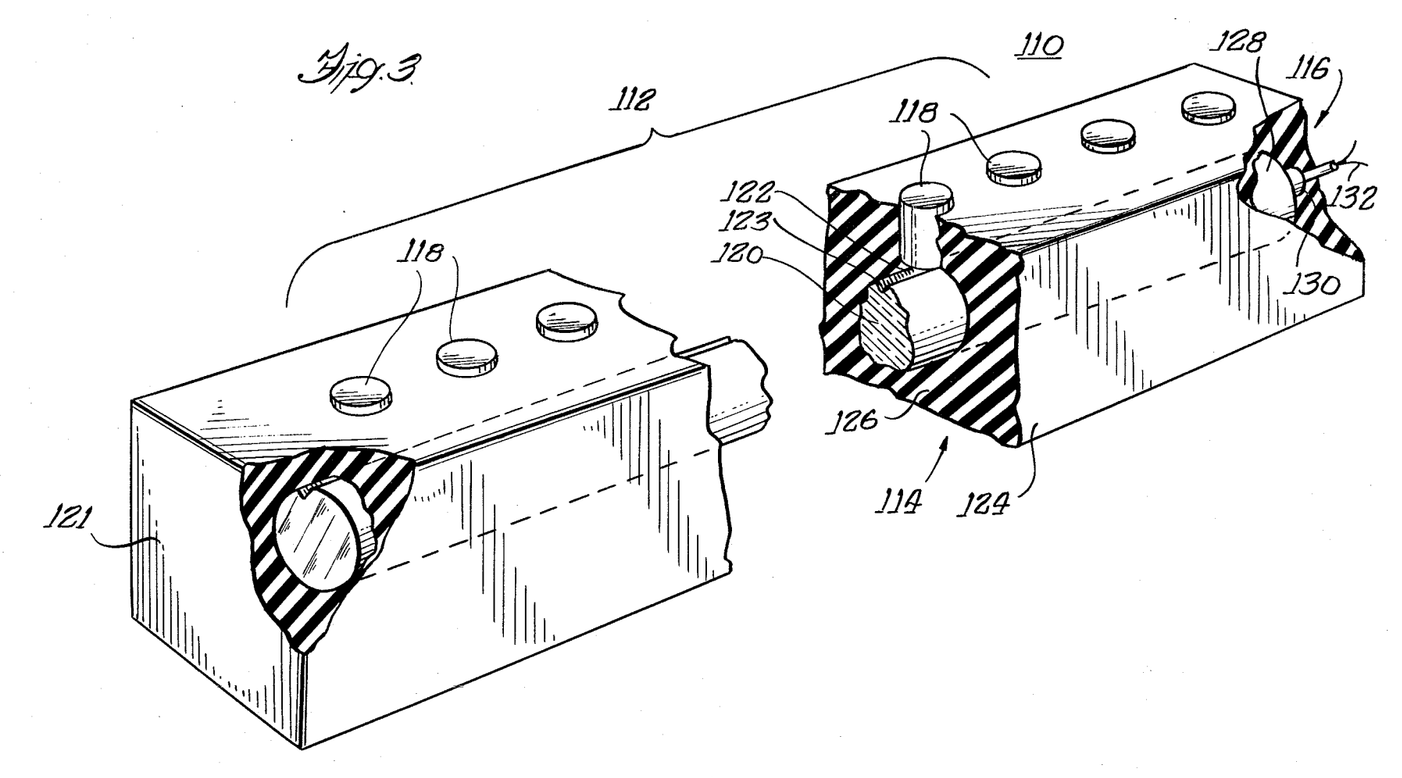
FIG. 3 is a fractional perspective view of another embodiment of the invention with portions broken away.

In FIG. 3, there is shown an elongated digital radiation sensor 110 having a radiation-collecting section 112, a housing 114, and a radiation-sensing section 116. The radiation-collecting section 112 and radiation-sensing section 116 are positioned within the housing 114 with the radiation-collecting section extending along a large portion of the housing and being aligned with the radiation-sensing section 116 which is located in one end of the housing 114.

To collect radiation and apply it to the radiation-sensing section 116, the radiation-collecting section 112 includes a plurality of radiation diffusers 118, an elongated transparent radiation conductor 120, and an air space 122 between the radiation diffusers 118 and the radiation conductors 120.

The air space 122 connects the top surface of the radiation conductor 120 along a majority of its length to the bottom of a plurality of the radiation diffusers 118, with the radiation diffusers 118 having a portion extending above the housing section 114 to receive radiation and a bottom portion positioned beneath the casing and in contact with the air space 122 to transmit diffused radiation against the surface of the radiation conductor 120.

The radiation diffusers 118 are generally plastic discs of Plexiglas or similar material with sufficient coloration to diffuse radiation that impinges upon them. The radiation conductor 120, in the preferred embodiment, is a quartz cylinder, but other elongated shapes of a solid transparent material may be used instead. Preferably it is grooved at 123 to permit radiation to enter.

To shield the radiation-collecting section 112 from stray radiation, the housing 114 includes an outer metallic casing 124 and an inner insulating material 126, with the outer metal casing being in the shape of an elongated tube having a square cross-section. The radiation conductors 120 is in the center of the housing and the insulating material is between the radiation conductor 120 and the metallic casing 124 except for the air space 122, the radiation diffusers 118 extending through the top portion of the casing 124 in a line with the longitudinal axis of the radiation conductor 120. An end piece 121 closes the end of the metallic casing 124 and is in contact with one end of the radiation conductor 120 to absorb radiation passing in that direction.

To sense the radiation collected by the radiation-collecting section 112, the radiation-sensing section 116 includes an optical unit 128 having within it a filter (not shown), a photocell 130 and a lens system to focus the radiation passing through the filter onto the photocell. The filter is positioned against the radiation conductor 120 between the photocell 130 and the end of the conductor so that the photocell receives radiation passing through the filter. The photocell 130 has the appropriate electrical wires 132 passing through an end portion of the metal casing 124 to provide an electrical signal indicative of the amount of radiation collected by the radiation-collecting section 112.

In use, radiation falls upon the radiation diffusers 118, which diffuse it and transmit it through the air space 122 to the radiation conductor 120. The radiation conductor 120 conducts it to the radiation-sensing section 116 where it is converted into electrical signals to indicate the amount of radiation incident upon the radiation sensor 110.

To diffuse radiation incident upon the radiation sensor 110, the radiation diffusers 118 include particles that diffuse radiation incident upon them and transmit the radiation to the air space 122 in a manner that follows Lambert's cosine law. The radiation diffusers 118 may include edge portions for cosine correction to make them more nearly follow Lambert's cosine law.

To conduct the radiation received by the radiation diffusers 118, the radiation conductor 120 transmits radiation entering its groove 123 in both directions along its axis toward the end piece 121 and the radiation-sensing section 116, with radiation being transmitted toward the end piece 121 being absorbed.

To sense the radiation received by the radiation diffusers 118, radiation passing from the end of the radiation conductor 120 is filtered by the filter so that a selected band of frequencies of radiation is passed to the photocell 130, resulting in an electrical signal on conductors 132 which indicate the amount of radiation incident upon the radiation diffusers 118. The use of the filter enables selected spectral bands to be monitored, which is useful in certain types of research.

While radiation diffusers 118 improve the performance of the radiation sensor 110, they are not absolutely necessary and radiation may pass through apertures or a slot into the radiation sensor and be received by the radiation conductor 120. Moreover, while a quartz rod is preferred because it transmits radiation at a desirable frequency, other types of transparent material may be used and, in some circumstances, the use of other materials is desirable to achieve different effects.

A digital sensor such as the radiation sensor 110 may be used to measure the density of a foliage as illustrated in the embodiment of FIGS. 1 and 2 or may be used to measure the area of a single scanned object as will be described in connection with FIG. 4. This type of measurement is used in agricultural research to determine the amount of radiation available for plant life, or to determine the area of leaf coverage by measuring the radiation flux beneath a canopy of leaves or under a particular leaf where the area of that leaf is to be measured. When used to measure a canopy with sunlight or a fixed source of radiation it operates in an analog rather than a digital mode.

Figure 4:
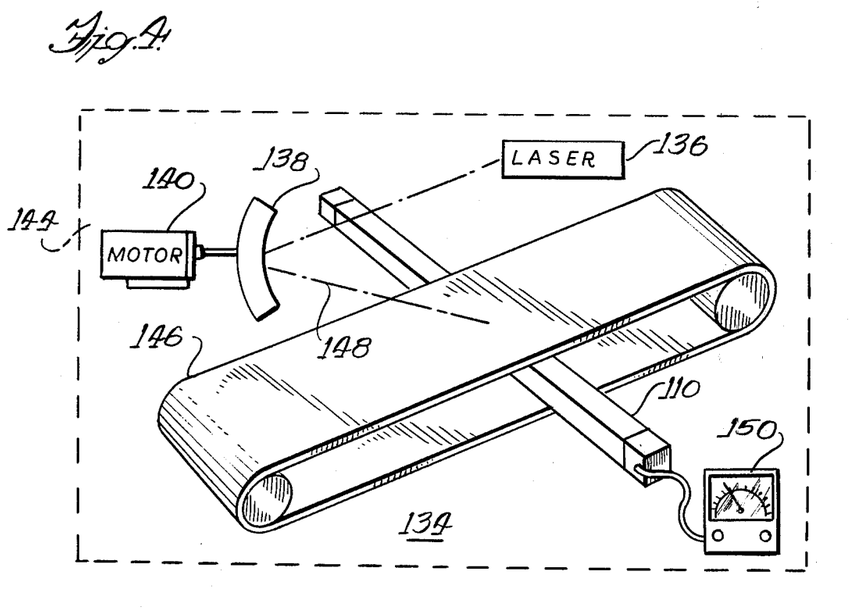
FIG. 4 is a simplified schematic diagram of apparatus comprising the embodiment of FIG. 3.

In FIG. 4, there is shown a scanning system 134, which is an apparatus in which the digital radiation sensor 110 is particularly useful and in which it operates in a digital mode. This scanning system has general utility but is especially useful in area meters, shown schematically at 144 in which an object is moved by a transparent conveyor 146 and scanned in the lateral direction by a beam of radiation 148. The scanning produces a plurality of counts on an instrument 150 indicating the area over which the beam of radiation 148 was blocked to prevent digitizing. This type of system is described in co-pending application Ser. No. 929,277, filed July 31, 1978, on Area Meter by Wurm et al. and assigned to the same assignee as this application.

The scanning system 134 includes a laser 136, a movable scanning mirror 138, a mirror pivoting system 140, and the radiation detector 110. The laser 136 is mounted to transmit either a continuous beam or a pulsed beam to the scanning mirror 138, which is pivoted by the mirror pivoting system 140 to direct the beam of radiation 148 from the laser 136 across the radiation diffusers 118 (FIG. 1) of the radiation detector 110.

In using the scanning system 134, the radiation beam 148 scans across the digital radiation sensor 110 generating a number of pulses on the conductors 132 representing the number of diffusers 118 which were scanned by the radiation beam 148. Accordingly, any objects positioned between the beam of radiation from the mirror 138 and the radiation detector 110 results in a reduction in the number of pulses transmitted through the conductors 132.

Because the number of pulses which are received by the counter 150 is constant when the digital radiation sensor 110 is not blocked from the beam of radiation scanned by the scanning mirror 138 and is reduced in number by a number corresponding to the number of radiation diffusers blocked by the object that is between the mirror 138 and the radiation sensor 110, the area of the object on the conveyor may be determined by subtracting the number of pulses counted from the maximum number of pulses for a given amount of travel of an unblocked conveyor. Other scanning and counting arrangements such as those described in the aforementioned patent application to Wurm et al may also be used without deviation from the invention. It is also possible to use a continuous groove and digitize by modulating the sensed signal with a pulse signal that represents the position of the scanning beam on the sensor.

It can be understood from the above description that the radiation sensor of this invention has the advantages of being simple and inexpensive. In one embodiment, it has the advantage of averaging radiation across a fixed length and in another embodiment of providing digital signals using a single sensing element in a scanning system.

Although preferred embodiments have been described in some detail, many modifications and variations in the invention are possible within the light of the above teachings. It is therefore to be understood that, within the scope of the appended claims, the invention may be practiced other than as specifically described.

What is claimed is:

1. Apparatus comprising:
    an elongated radiation conductor having first and second ends;
    means for transmitting radiation into said elongated radiation conductor in a predetermined path along a substantial portion of its length;
    said means for transmitting radiation into said elongated radiation conductor including cosine-corrected radiation diffusing means positioned adjacent to said radiation conductor, whereby radiation is cosine corrected and diffused and the diffused cosine-corrected radiation enters said radiation conductor and travels to at least one of said first and second ends thereof;
    radiation sensing means mounted adjacent to said one end to measure said radiation;
    housing means for enclosing said elongated radiation detector except for said cosine-corrected diffusing means;
    said housing including a bottom mounting surface and a top opening for receiving said cosine-corrected diffusing means, whereby said radiation conductor may be mounted with the cosine-corrected diffusing means facing upwardly to receive sunlight;
    filter means for passing only light within the spectrum of sunlight;
    said filter means including a replaceable filter mounted between said one end and said radiation sensing means, whereby only light within the frequency spectrum of sunlight is transmitted to said radiation sensing means;
    an ammeter; and
    said radiation sensing means including means for converting light to an electrical signal and transmitting the electrical signal to said ammeter, whereby said ammeter indicates units of light reaching said cosine-corrected diffusing means.

2. Apparatus according to claim 1 in which said radiation conductor is a quartz rod.

3. Apparatus according to claim 2 in which said quartz rod is at least one meter in length and said means for transmitting radiation into said elongated radiation conductor includes a longitudinally extending groove in a surface of said radiation conductor.

4. Apparatus according to claim 3 in which said diffusing means comprises a single elongated diffuser positioned adjacent to said means for transmitting radiation.

5. Apparatus according to claim 3 in which said radiation diffusing means comprises:
    a plurality of spaced apart diffusing means; and
    said spaced apart diffusing means being positioned in accordance with a regular pattern and being separated from each other by opaque members or non-diffusing members.

6. Apparatus according to claim 5 further including means for scanning a beam of radiation across said plurality of diffusers.

7. Apparatus according to claim 1 in which said radiation diffusing means comprises:
    a plurality of spaced apart diffusing means; and
    said spaced apart diffusing means being positioned in accordance with a regular pattern and being separated from each other by opaque members or non-diffusing members.

8. Apparatus according to claim 7 further including means for scanning a beam of radiation across said plurality of diffusers.

9. Apparatus according to claim 1 in which said filter has a band pass range of between 400 and 700 nanometers.

10. Apparatus comprising:
    an elongated radiation conductor having first and second ends;
    means for transmitting radiation into said elongated radiation conductor in a predetermined path along a substantial portion of its length;
    said means for transmitting radiation into said elongated radiation conductor including radiation diffusing means positioned adjacent to said radiation conductor, whereby radiation is diffused and the diffused radiation enters said radiation conductor and travels to at least one of said first and second ends thereof;
    radiation sensing means mounted adjacent to said one end to measure said radiation;
    a replaceable filter mounted between said one end and said radiation sensor;
    said radiation conductor being a quartz rod;
    said quartz rod being at least one meter in length and said means for transmitting radiation into said elongated radiation conductor including a longitudinally extending groove in a surface of said radiation conductor;
    a plurality of spaced apart diffusing means;

said spaced apart diffusing means being positioned in accordance with a regular pattern and being separated from each other by opaque members or non-diffusing members;

means for scanning a beam of radiation across said plurality of diffusers; and means for moving an object, the area of which is to be measured, between said means for applying a beam of radiation and said diffusers, whereby pulses are generated indicating a relationship to the area of said object.

11. Apparatus according to claim 10 in which said filter has a band pass range of between 400 and 700 nanometers.

12. Apparatus according to claim 11 in which said radiation conductor is a quartz rod.

13. Apparatus according to claim 12 in which said quartz rod is at least one meter in length and said means for transmitting radiation into said elongated radiation conductor includes a longitudinally extending groove in a surface of said radiation conductor.

14. A method of measuring density of a foliage canopy comprising the steps of:

placing an elongated radiation sensor beneath said foliage;

defusing radiation incident on said elongated sensor after it passes through said foliage;

transmitting said diffused radiation into an elongated radiation conductor;

receiving radiation from one end of said radiation conductor;

converting the radiation received on said one end of said radiation conductor into an electrical signal;

measuring said electrical signal; and correlating the measurement of said electric signal and the length of said sensor receiving said radiation with the density of foliage.

15. A method in accordance with claim 14 in which said step of transmitting radiation to said radiation conductor includes the step of transmitting radiation through a groove in said radiation conductor one meter long into said radiation conductor.

16. A method according to claim 15 in which the step of receiving radiation from said one end of said radiation conductor includes the step of transmitting said radiation to a photocell.

17. A method according to claim 16 in which the step of transmitting said radiation to a photocell includes the step of transmitting only a selected waveband of radiation to said sensor, whereby only radiation capable of being absorbed by plant life is measured.

18. A method according to claim 14 in which the step of receiving radiation from said one end of said radiation conductor includes the step of transmitting said radiation to a photocell.

19. A method according to claim 18 in which the step of transmitting said radiation to a photocell includes the step of transmitting only a selected waveband of radiation to said sensor, whereby only radiation capable of being absorbed by plant life is measured.

20. Apparatus comprising:

an elongated radiation conductor having first and second ends;

means for transmitting radiation into said elongated radiation conductor in a predetermined path along a substantial portion of its length;

said means for transmitting radiation into said elongated radiation conductor including radiation diffusing means positioned adjacent to said radiation conductor, whereby radiation is diffused and the diffused radiation enters said radiation conductor and travels to at least one of said first and second ends thereof;

radiation sensing means mounted adjacent to only one of said ends to measure said radiation; and means for absorbing radiation positioned adjacent to the other of said first and second ends of said elongated radiation conductor, whereby radiation transmitted along said radiation conductor in the direction opposite to said radiation sensing means is absorbed, and not sensed by said radiation sensing means.

21. Apparatus according to claim 20 in which said means for absorbing radiation includes a roughened surface on said other of said first and second ends of said elongated radiation conductor and radiation absorbing material on said roughened surface.

22. Apparatus comprising:

an elongated radiation conductor having first and second ends;

means for transmitting radiation into said elongated radiation conductor in a predetermined path along a substantial portion of its length;

said means for transmitting radiation into said elongated radiation conductor including radiation diffusing means positioned adjacent to said radiation conductor, whereby radiation is diffused and the diffused radiation enters said radiation conductor and travels to at least one of said first and second ends thereof;

radiation sensing means mounted adjacent to said one end to measure said radiation;

means for causing the sensitivity to received radiation of said radiation sensing means to respond substantially equally to the same intensity of radiation transmitted into said elongated radiation conductor at any point along its length;

said means for causing the sensitivity to received radiation to be substantially uniform including variations in the shape of said radiation diffusing means, tailored at different points along its length to remove non-uniformities in the diffusing means, whereby said radiation sensing means responds substantially equal to the same intensity of radiation at any point along the length of the radiation conductor.

23. Apparatus comprising:

an elongated radiation conductor having first and second ends;

means for transmitting radiation into said elongated radiation conductor in a predetermined path along a substantial portion of its length;

said means for transmitting radiation into said elongated radiation conductor including radiation diffusing means positioned adjacent to said radiation conductor, whereby radiation is diffused and the diffused radiation enters said radiation conductor and travels to at least one of said first and second ends thereof;

radiation sensing means mounted adjacent to said one end to measure said radiation; and means for causing the sensitivity to received radiation of said radiation sensing means to respond substantially equally to the same intensity of radiation transmitted into said elongated radiation conductor at any point along its length; and said means for causing the sensitivity to received radiation of said radiation sensing means to respond substantially equally including means for causing only a portion of the radiation emitted from said one end to be passed to said sensing means.

24. Apparatus according to claim 23 in which said means for causing only a portion includes means for causing only a portion within a predetermined cone and containing predominately flux which has a pitch such that the number of lossy bounces is low is passed to said sensing means.

25. Apparatus according to claim 24 in which said means for causing only a portion includes means for transmitting only radiation which has an angle of incidence of 40 degrees or less within said radiation conductor.

26. Apparatus according to claim 25 in which said means for causing equality of said sensed radiation includes means for absorbing radiation at selected locations along said means for transmitting radiation into said elongated radiation conductor.

27. A method for manufacturing an average radiation sensor comprising the steps of:
preparing a radiation conductor;
preparing along one side of said radiation conductor diffusing means for transmitting radiation into said radiation conductor;
positioning at one end of said radiation conductor a sensing means for sensing radiation transmitted into said radiation conductor along said diffusing means; and
the step of preparing said diffusing means comprising the steps of: transmitting radiation into said diffusing means at locations starting adjacent to said sensing means and moving away from said sensing means along said diffusing surface; measuring the intensity of the radiation transmitted to said sensing means; and adjusting said diffusing means to cause a uniform proportion of the radiation transmitted to the diffusing means to reach said sensor at each location, whereby said sensitivity of said sensing means is uniform along its length.

28. A method for manufacturing an average radiation sensor comprising the steps of:
preparing a radiation conductor;
preparing along one side of said radiation conductor diffusing means for transmitting radiation into said radiation conductor;
positioning at one end of said radiation conductor a sensing means for sensing radiation transmitted into said radiation conductor along said diffusing means;
the step of preparing said diffusing means comprising the steps of: transmitting radiation into said diffusing means at locations starting adjacent to said sensing means and moving away from said sensing means along said diffusing surface; measuring the intensity of the radiation transmitted to said sensing means; and adjusting said diffusing means to cause a uniform proportion of the radiation transmitted to the diffusing means to reach said sensor at each location, whereby said sensitivity of said sensing means is uniform along its length; and
roughing the other end of said radiation conductor from said sensing means or coating it with an absorbing material.

29. The method of claim 28 further comprising the step of positioning a lens between said sensor and said radiation conductor to cause only radiation leaving at a predetermined angle or less to be applied to said radiation sensing means.

30. A method according to claim 29 in which said step of positioning said lens between said sensing means and said radiation conductor includes the step of positioning a lens which applies only radiation having an angle of incidence from the normal of 75 degrees or greater to the interior surface of said radiation conductor as it traverses said radiation conductor.

31. A method according to claim 30 in which the step of adjusting said diffusing means including the step of adding scratches to increase the sensitivity of said elongated conductor at selected points.

32. A method according to claim 31 in which the step of equalizing said response includes the step of adding absorbing material at selected points along the length of said diffuser to reduce the sensitivity at said points.

33. Apparatus comprising:
an elongated radiation conductor having first and second ends;
means for transmitting radiation into said elongated radiation conductor in a predetermined path along a substantial portion of the length;
said means for transmitting radiation into said elongated radiation conductor including radiation diffusing means positioned adjacent to said radiation conductor, whereby radiation is diffused and the diffused radiation enters said radiation conductor and travels to at least one of said first and second ends thereof;
radiation sensing means mounted adjacent to said one end to measure said radiation;
said radiation diffusing means comprising a plurality of spaced apart diffusing means, said spaced apart diffusing means being positioned in accordance with a regular pattern and being separated from each other by sections which are incapable of diffusing light for transmission into said elongated radiation conductor;
means for scanning a beam of radiation across said plurality of diffusers; and
means for moving an object, the area of which is to be measured, and said diffusers with respect to each other whereby pulses are generated indicating a relationship to the area of said object.

34. A method for manufacturing an average radiation sensor comprising the steps of:
preparing a radiation conductor;
preparing along one side of said radiation conductor diffusing means for transmitting radiation into said radiation conductor;
positioning at one end of said radiation conductor a sensing means for sensing radiation transmitted into said radiation conductor along said diffusing means; and
positioning a lens between said sensor and said radiation conductor to cause only radiation leaving at a predetermined angle or less to be applied to said radiation sensing means.

* * * * *

UNITED STATES PATENT AND TRADEMARK OFFICE
CERTIFICATE OF CORRECTION

PATENT NO. : 4,264,211
DATED : April 28, 1981
INVENTOR(S) : William W. Biggs

It is certified that error appears in the above—identified patent and that said Letters Patent is hereby corrected as shown below:

Column 2, line 43, change "applica-" to --application--.

Column 2, line 65, change "india" to --India--.

Column 3, line 33, change "make thems" to --makes them--.

Column 3, line 42, change "use" to --user--.

Column 4, line 62, change "pleriglas" to --Plexiglas--.

Column 5, line 37, change "tapped.  One" to --tapped, one--.

Column 7, line 36, change "pleriglas" to --Plexiglas--.

Column 8, line 9, change "india" to --India--.

Column 9, line 20, change "conductors" to --conductor--.

UNITED STATES PATENT AND TRADEMARK OFFICE
CERTIFICATE OF CORRECTION

PATENT NO. : 4,264,211
DATED : April 28, 1981
INVENTOR(S) : William W. Biggs

It is certified that error appears in the above—identified patent and that said Letters Patent is hereby corrected as shown below:

Column 9, line 42, change "conductors" to --conductor--.

Column 14, line 34, after "radiation;" insert --and--.

Column 14, line 46, change "equal" to --equally--.

Signed and Sealed this

Twenty-eighth Day of July 1981

[SEAL]

Attest:

Attesting Officer

GERALD J. MOSSINGHOFF

Commissioner of Patents and Trademarks